(12) United States Patent
Paetz et al.

(10) Patent No.: US 8,703,203 B2
(45) Date of Patent: Apr. 22, 2014

(54) ORAL DOSAGE FORM OF DEFERASIROX

(75) Inventors: Jana Paetz, Bonn (DE); Katrin Rimkus, Pullach (DE)

(73) Assignee: ratiopharm GmbH, Ulm (DE)

( * ) Notice: Subject to any disclaimer, the term of this patent is extended or adjusted under 35 U.S.C. 154(b) by 0 days.

(21) Appl. No.: 13/807,738

(22) PCT Filed: Jul. 7, 2011

(86) PCT No.: PCT/EP2011/003387
§ 371 (c)(1),
(2), (4) Date: Feb. 21, 2013

(87) PCT Pub. No.: WO2012/003987
PCT Pub. Date: Jan. 12, 2012

(65) Prior Publication Data
US 2013/0142871 A1 Jun. 6, 2013

(30) Foreign Application Priority Data
Jul. 8, 2010 (EP) .................................. 10007059

(51) Int. Cl.
*A61K 9/16* (2006.01)
(52) U.S. Cl.
USPC ............................ 424/493; 424/409; 424/489
(58) Field of Classification Search
USPC ................................................ 424/465–489
See application file for complete search history.

(56) References Cited

U.S. PATENT DOCUMENTS 6,649,186 B1 * 11/2003 Robinson et al. ............. 424/466
2004/0265375 A1 * 12/2004 Platteeuw et al. ............ 424/464

FOREIGN PATENT DOCUMENTS

| WO | WO 03/072084 A1 | 9/2003 |
| WO | WO 2004035026 A1 * | 4/2004 |
| WO | WO 2005/097062 A1 | 10/2005 |
| WO | WO 2009/016359 A1 | 2/2009 |
| WO | WO 2009/135948 A2 | 11/2009 |

OTHER PUBLICATIONS

PCT/EP2011/003387, Int'l Preliminary Report on Patentability (Ch. II), Oct. 25, 2012.
PCT/EP2011/003387, Written Opinion, Oct. 20, 2011.
PCT/EP2011/003387, Int'l Search Report, Oct. 20, 2011.

\* cited by examiner

*Primary Examiner* — Michael G Hartley
*Assistant Examiner* — Micah-Paul Young
(74) *Attorney, Agent, or Firm* — Milstein Zhang & Wu LLC

(57) ABSTRACT

The invention relates to an oral dosage form containing deferasirox, binder, disintegrant and optionally wicking agent, wherein the introduction of the dosage form into water leads to a suspension wherein the suspended particles have an average particle size (D50) of 20 µm to 120 µm, and also to a method of producing it.

19 Claims, No Drawings

ORAL DOSAGE FORM OF DEFERASIROX

The invention relates to an oral dosage form containing deferasirox, binder, disintegrant and optionally wicking agent, wherein the introduction of the dosage form into water leads to a suspension wherein the suspended particles have an average particle size (D50) of 20 µm to 120 µm, and also to a method of producing it.

Deferasirox is used to treat chronic iron overload (excess iron in the body), which is caused by repeated blood transfusions.

The IUPAC name for deferasirox is 4-[(3Z,5E)-3,5-bis(6-oxo-1-cyclohexa-2,4-dienylidene)-1,2,4-triazolidine-1-yl] benzoic acid. The chemical structure of deferasirox is shown in formula (1) below:

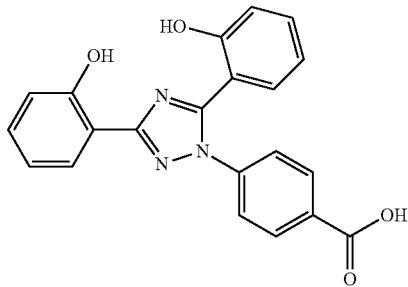 [SMILES: O=C(O)c1ccc(-n2nc(-c3ccccc3O)nc2-c2ccccc2O)cc1]

In the context of this invention, the term "deferasirox" encompasses a compound in accordance with formula (I) or pharmaceutically acceptable salts and solvates and/or hydroates thereof. The synthesis of deferasirox is described in, for example, the international patent application WO 97/49395.

Deferasirox is a substance which is poorly soluble in water and, in addition, has bad tableting properties (see WO 2007/045445, page 2, third paragraph). In the state of the art, various proposals have been made on how to formulate deferasirox.

WO 2009/106824 A2 describes effervescent tablets containing deferasirox. Effervescent tablets are, however, unpopular with many patients and may in some cases lead to reduced compliance with the therapy.

WO 2004/035026 A1 discloses tablets which disintegrate in water and which preferably contain 28% to 32% deferasirox and 10% to 35% disintegrant. It has, however, transpired that the formulation proposed in WO 2004/035026 A1 is not ideal with regard to the stability of the resulting suspension, especially if the suspension is not taken immediately, but only after a certain time (as frequently happens, because patients dissolve the tablet but then forget to take it).

The object of the invention was therefore to provide an improved pharmaceutical formulation for the oral administration of deferasirox. In particular, the intention is to provide an improved dosage form which is capable of being taken advantageously as an aqueous suspension.

It has unexpectedly been found that improved oral dosage forms can be provided if the excipients are selected such that the administration of the dosage form in water leads to a suspension with a specific particle size.

In particular, it has been found that a specific content of disintegrant or a specific ratio of disintegrant to active agent solves the problem advantageously.

Normally, disintegrants are used to cause a tablet to disintegrate quickly and thus to release the active agent from the tablet in a short time. They are usually employed in a concentration of 15%, in exceptional cases up to 20%. [Die Tablette, W. A. Ritschel, A. Bauer-Brandl]. It has now surprisingly been found that deferasirox can advantageously be formulated in a tablet that disintegrates very quickly if the proportion of disintegrant is more than 35%.

The high proportion of disintegrant has a positive effect on the deposition of the particles and the distribution of the particles in water, so that a stable suspension can be obtained even after storage.

It is remarkable that no gums or even polyhydric alcohols have to be added in order to increase the viscosity of the suspension medium, so that in the composition of the invention, even without adding them, sedimentation is counteracted and in this way stable suspensions can be obtained. ["Pharmazeutische Technologie", Rudolf Voigt]

This effect can thus unexpectedly be achieved with a high proportion of disintegrant, which leads to a stable suspension. Thanks to the high concentration of the disintegrant, intermolecular interactions arise in the formulation, which have a positive influence on the sedimentation rate.

Furthermore, it has surprisingly been found in the present invention that despite the high content of disintegrant, tablets with advantageous hardness and friability can be obtained. For a person skilled in the art, this was unexpected because it is known, e.g. from WO 2008/104996 (see page 3, last paragraph to page 4, second paragraph) that in dispersion tablets, the addition of disintegrant weakens the tablet structure and has a very negative influence on both the hardness and the friability. For this reason, WO 2008/104996 proposes dispersion tablets without any disintegrant at all. Similarly, WO 2007/045445 proposes dispersion tablets of deferasirox with a very low content of 4% to 6% disintegrant.

In addition, it has been found that the use of a granulation process, especially a melt granulation process (or alternatively a specific wet granulation process), permits advantageous deferasirox dosage forms.

The subject matter of the invention is therefore an oral dosage form containing
(a) deferasirox
(b) binder
(c) disintegrant, and
(d) optionally wicking agent
wherein introducing the dosage form into water leads to a suspension wherein the suspended particles have an average particle size (D50) of 20 µm to 120 µm.

The oral dosage form is preferably a solid oral dosage form, especially a tablet or granules, wherein the granules may be filled in sachets or capsules. Alternatively, the oral dosage form may also be present in the form of a dry syrup. The oral dosage form is particularly preferably present in the form of a tablet. In particular the tablet of the invention has a disintegration time of 10 to 90 seconds, more preferably 20 to 60 seconds. The disintegration time is preferably determined in accordance with Ph. Eur. 6.0, section 2.9.1, Test A at 35° C.

The oral dosage form of the invention can be administered perorally. It is, however, preferable for the dosage form of the invention to be suspended in water and for the resulting suspension to be administered. In accordance with the invention, introducing the dosage form into water leads to a suspension. The suspension contains water and optionally components of the dosage form of the invention dissolved therein, and also solid (i.e. non-dissolved) components of the dosage form of the invention. In accordance with the invention, the suspended particles (i.e. the solid, non-dissolved components) have an average particle size (D50) of 20 µm to 150 µm, preferably 45 µm to 120 µm, more preferably 50 µm to 110

μm, even more preferably 55 μm to 100 μm, particularly preferably 60 μm to 95 μm and especially 65 μm to 90 μm.

In order to determine the particle size specified, the composition of the invention is dissolved in 150 ml water (Aqua purificata in accordance with Ph. Eur) at 25° C. The particle size is determined 5 minutes after the dosage form is introduced into the water. During those 5 minutes, the suspension is stirred, preferably at 50 revolutions per minute.

The "particle size" of a particle to be determined is understood for the purposes of the invention to mean the diameter of an equivalent particle which is assumed to be spherical and to have the same light-scattering pattern as the particles to be determined. In this application, the particle size is determined by means of laser diffractometry. Specifically, a Malvern Instruments Mastersizer 2000 (Software Version 5.54) was used to determine the particle size. $H_2O$ (ultrapure) is preferably used as the medium, shading 10 to 30% (especially 20%) and a stirring speed of 2,500 r.p.m. The sample is prepared with minutes of stirring, followed by 2 minutes in an ultrasonic bath at 100%. The sample is added until the shading is in the desired range.

The evaluation is performed using the Fraunhofer method.

"Particle size distribution of the intermediate" is to be understood in the context of this invention as meaning the statistical distribution of the volume portions based on all the particle sizes of the particles of the intermediate. "Volume portion" means the volume-based proportion in percent of all particles with a defined particle size. The D50 value of the particle size distribution describes the particle size at which 50% by volume of the particles have a smaller particle size than the particles corresponding to the D50 value. Likewise, 50% by volume of the particles then have a larger particle size than the D50 value. The D50 value is also referred to as the "average particle size".

The D90 value of the particle size distribution accordingly describes the particle size at which 90% by volume of the particles have a smaller particle size than the particle size corresponding to the D90 value.

The D10 value of the particle size distribution analogously describes the particle size at which 10% by volume of the particles have a smaller particle size than the particle size corresponding to the D10 value.

In a preferred embodiment, the suspension usually has solid particles with a D10 value of between 2.0 μm and 50 μm, preferably between 3.0 μm and 20 μm.

In one preferred embodiment, the suspension usually has solid particles with a D90 value between 70 μm and 350 μm, preferably between 100 μm and 220 μm.

The ratio of D50 value to D10 value in the suspension is usually 25:1 to 2:1, preferably 15:1 to 3:1. The ratio of D90 value to D50 value in the suspension is usually 10:1 to 2:1, preferably 4.5:1 to 3:1.

It has been shown that a specific content of disintegrant or a specific ratio of disintegrant to active agent in the oral dosage form of the invention is particularly advantageous.

A preferred subject matter of the invention is therefore an oral dosage form containing
(a) deferasirox
(b) binder
(c) disintegrant and
(d) optionally wicking agent
wherein the dosage form contains more than 35% by weight, disintegrant (c), more preferably more than 40% by weight, particularly preferably 42 to 60% by weight, especially 45 to 55% by weight disintegrant (c), based on the total weight of the dosage form, and/or
wherein the weight ratio deferasirox:disintegrant is 1.0:1.0 to 1.0:3.0, preferably 1.0:1.1 to 1.0:2.5, more preferably 1.0:1.2 to 1.0:2.0. When introduced into water, this composition of the invention preferably leads to a suspension with the above-mentioned particle size distribution of the non-dissolved components.

The oral dosage form of the invention also contains preferably 10 to 50% by weight, more preferably 20 to 35% by weight deferasirox (a), based on the total weight of the dosage form.

In addition, the oral dosage form of the invention contains preferably 1 to 25% by weight, more preferably 2 to 10% by weight binder (b), based on the total weight of the dosage form.

Furthermore, the oral dosage form of the invention contains preferably 5 to 25% by weight, more preferably 10 to 20% by weight wicking agent (d), based on the total weight of the dosage form.

Apart from the components (a) to (d), the dosage form of the invention may also contain fillers (e), wetting agents and optionally further pharmaceutical excipients. The oral dosage form of the invention preferably contains 5 to 35% by weight, more preferably 10 to 20% by weight filler (e), based on the total weight the dosage form. The oral dosage form of the invention preferably contains 0.1 to 5% by weight, more preferably 0.5 to 3% by weight wetting agent (f), based on the total weight the dosage form.

In a particularly preferred embodiment, the oral dosage form of the invention thus contains:
(a) 10 to 50% by weight, more preferably 20 to 35% by weight deferasirox,
(b) 1 to 25% by weight, more preferably 2 to 10% by weight binder,
(c) more than 35% by weight, more preferably more than 40% by weight, particularly preferably 42 to 60% by weight disintegrant,
(d) 5 to 25% by weight, more preferably 10 to 20% by weight wicking agent,
(e) 5 to 35% by weight, more preferably 10 to 20% by weight filler,
(f) 0.1 to 5% by weight, more preferably 0.5 to 3% by weight wetting agent,
wherein the weight ratio deferasirox:disintegrant is especially 1.0:1 to 1:3.0, preferably 1.1:2.5, more preferably 1.2:2.0.

The components (a) to (f) will be explained in more detail below.

Deferasirox (a) is preferably used in the form of the free acid, i.e. preferably not in the form of a pharmaceutically acceptable salt.

The deferasirox employed usually has an average particle size (D50) of 1 μm to 150 μm, preferably 5 μm to 100 μm, more preferably 10 μm to 80 μm, especially 15 μm to 70 μm (measured in accordance with the light scattering method described above).

In a preferred embodiment, the deferasirox used in the dosage form per se or a pharmaceutically acceptable salt thereof used in the dosage form has a water content of 0.01 to 10% by weight, more preferably 0.25 to 8.0% by weight, particularly preferably 0.4 to 6.0% by weight and especially 0.6 to 4.0% by weight. In the context of this application, the water content is preferably determined according to the Karl Fischer method, using a coulometer at 160° C. A Metrohm 831 KF coulometer with a titration cell without a diaphragm is preferably used. Usually, a 20 mg sample of deferasirox is analysed.

In the context of this invention, the binder (b) is generally a substance which is capable of increasing the strength of the resulting dosage form, especially the resulting tablets.

The binder (b) may be a hydrophilic polymer, especially a hydrophilic thermoplastic polymer or mixtures thereof. Hydrophilic polymers are polymers which possess hydrophilic groups. Examples of suitable hydrophilic groups are hydroxy, amino, carboxy and sulphonate. In addition, the preferably hydrophilic polymer which can be used for the preparation of the intermediate preferably has a weight-average molecular weight of 1,000 to 150,000 g/mol, more preferably from 2,000 to 90,000 g/mol, especially 2,500 to 75,000 g/mol. The weight-average molecular weight is determined in the context of this application by means of gel permeation chromatography.

When the polymer used as the binder (b) is dissolved in water in an amount of 2% by weight, the resulting solution preferably has a viscosity of 0.1 to 50 mPa·s, more preferably 1.0 to 8 mPa·s, especially 1 to 5.0 mPa·s, measured at 25° C. and determined in accordance with Ph. Eur., 6th edition, chapter 2.2.10.

In addition to this, a hydrophilic polymer used as a binder preferably has a glass transition temperature ($T_g$) and/or a melt temperature ($T_s$) of at least 20° C., preferably higher than 20° C. to 220° C., more preferably 40° C. to 180° C., even more preferably 40° C. to 100° C. The glass transition temperature is the temperature at which the hydrophilic polymer becomes brittle when cooling down and soft when being heated. This means that hydrophilic polymers become soft at temperatures higher than the glass transition temperature ($T_g$) and become plastically deformable without breaking. The glass transition temperature or the melt temperature is determined by means of a Mettler-Toledo® DSC1, applying a heating rate of 10° C. per minute and a cooling rate of 15° C. per minute. The determination method is based essentially on Ph. Eur. 6.1, Chapter 2.2.34. In order to determine the $T_g$ or the $T_s$. the polymer is heated twice (i.e. heated, cooled, heated).

The dosage form of the invention may, for example, comprise the following hydrophilic polymers as binders (b): polysaccharides, such as hydroxypropyl methyl cellulose (HPMC), polyvinyl pyrrolidone, polyvinyl alcohol, polymers of acrylic acid and their salts, polyacrylamide, polymethacrylates, vinyl pyrrolidone/vinyl acetate copolymers (such as Kollidon® VA64, BASF), polyalkylene glycols, such as polypropylene glycol or preferably polyethylene glycol, co-block polymers of polyethylene glycol, especially co-block polymers of polyethylene glycol and polypropylene glycol (Pluronic®, BASF), and mixtures of the polymers mentioned.

It is preferable to use as the binder (b): hydroxypropyl methyl cellulose (HPMC), preferably with a weight-average molecular weight of 20,000 to 90,000 g/mol and/or preferably a proportion of methyl groups of 10 to 35%; hydroxypropyl cellulose (HPC), preferably with a weight-average molecular weight of 40,000 to 100,000 g/mol, polyvinyl pyrrolidone, preferably with a weight-average molecular weight of 10,000 to 60,000 g/mol, especially 12,000 to 40,000 g/mol, copolymer of vinyl pyrrolidone and vinyl acetate, especially with a weight-average molecular weight of 40,000 to 75,000 g/mol, polyethylene glycol, especially with a weight-average molecular weight of 2,000 to 50,000 g/mol, polyoxyethylene alkyl ether and/or polyvinyl alcohol, preferably with a weight-average molecular weight of 1,000 to 50,000 g/mol. Polyvinyl pyrrolidone is particularly preferably used, especially with the above-mentioned molecular weight.

"Disintegrants" (c) is the term generally used for substances which accelerate the disintegration of a dosage form, especially a tablet, after it is placed in water. Suitable disintegrants are, for example, organic disintegrants such as carrageenan, alginic acid, sodium alginate, maize starch, pregelatinised starch, sodium carboxymethyl starch, calcium carboxymethyl starch, crosslinked carboxymethyl cellulose, preferably as the sodium salt (croscarmellose) and/or crosslinked polyvinyl pyrrolidone (crospovidone). In addition, inorganic disintegrants such as bentonites can be used. Alkaline disintegrants can likewise be used. The term "alkaline disintegrants" means disintegrants which, when dissolved in water, produce a pH level of more than 7.0, such as sodium bicarbonate for example. Mixtures of the above-mentioned disintegrants can also be used.

Crospovidone and/or croscarmellose are particularly preferably used as disintegrants, especially in the above-mentioned amounts.

The disintegrant (c) employed preferably has an average particle size (D50) of 30 to 160 µm, more preferably 50 to 150 µm, particularly preferably 70 to 130 µm (determined by means of laser diffractometry as described above).

In general a wicking agent (d) is a substance with the ability to draw up a biological fluid (preferably water) into a solid (preferably into the dosage form of the invention, preferably by means of physisorption). Physisorption is defined as a form of adsorption in which the liquid molecules can adhere to the surface of the wicking agent, preferably by means of van der Waals binding between the surface of the wicking agent and the adsorbed fluid molecule (preferably water). Normally a wicking agent achieves this with or without swelling. Normally, a non-swelling wicking agent which attracts water will ultimately have a volume consisting substantially of the volume of the wicking agent and the amount of water which it attracts. In general, a swelling wicking agent will have a volume consisting substantially of the volume of the wicking agent, the amount of water which it attracts, and an additional volume, caused by steric and molecular forces.

In the oral dosage form of the invention, preferably a tablet, the wicking agent (d) preferably causes the formation of channels or pores. This facilitates the penetration of the water molecules into the dosage form, especially by physisorption. The function of the wicking agent therefore consists in transporting water to the surfaces inside the dosage form in order in this way to create channels in or a network on an enlarged surface. The wicking agents (d) employed preferably have an average particle size (D50) of 30 to 160 µm, more preferably 50 to 150 µm, particularly preferably 70 to 130 µm (determined by means of laser diffractometry as described above).

Examples of wicking agents used are: microcrystalline cellulose, silicified microcrystalline cellulose, colloidal silica, kaolin, titanium dioxide, fumed silica, aluminium, niacinamide, M-Pyrol, bentonite, magnesium-aluminium silicate, polyester, polyethylene, or mixtures thereof. The wicking agents of the pharmaceutical composition of the present invention preferably contain cellulose and cellulose derivatives, such as silicified microcrystalline cellulose, colloidal silica, and mixtures thereof. The silicified microcrystalline cellulose preferably used is commercially obtainable under the trade name Prosolv® and has a silica content of 1 to 3% by weight, preferably 2% by weight. In this application, lactose does not count as a wicking agent.

The oral dosage form of the invention, especially a tablet, may also contain fillers (e). "Fillers" generally means substances which serve to form the body of the tablet in the case of tablets with small amounts of active agent (e.g. less than 60% by weight). This means that fillers "dilute" the active agents in order to produce an adequate tablet-compression mixture. The normal purpose of fillers, therefore, is to obtain a suitable tablet size. The fillers (e) employed preferably have an average particle size (D50) of 30 to 160 µm, more preferably 50 to 150 µm, particularly preferably 70 to 130 µm (determined by means of laser diffractometry as described above).

Examples of preferred fillers are lactose, lactose derivatives, starch, starch derivatives, treated starch, chitin, cellulose and derivatives thereof, calcium phosphate, sucrose, calcium carbonate, magnesium carbonate, magnesium oxide, maltodextrin, calcium sulphate, dextrates, dextrin and/or dextrose, hydrogenated vegetable oil.

It is particularly preferable to use lactose monohydrate as the filler. In particular, spray-dried lactose monohydrate is used as the filler. This preferably has a D10 value of the average particle size distribution (determined by means of laser diffractometry as described above) of 20 to 40 µm, a D50 value of 60 to 130 µm and a D90 value of 150 to 300 µm. In addition, spray-dried lactose monohydrate preferably has a bulk density of 550 to 650 g/l and a tapped density of 675 to 775 g/l.

Other fillers that can be used are sugar alcohols and/or disaccharides, such as mannitol, sorbitol, xylitol, isomalt, glucose, fructose, maltose and mixtures thereof. The term "sugar alcohols" in this context also includes monosaccharides.

The oral dosage form of the invention, especially a tablet, may also contain wetting agents (f). "Wetting agents" is the term generally used to describe one or more substances that have both lipophilic and hydrophilic properties. Because of this amphiphilic property, wetting agents can reduce or prevent the occurrence of difficulties during and after the processing of hydrophobic active agents or excipients, such as excessive drying out during the storage or capping of tablets. Wetting agents can be subdivided into anionic surface-active agents, amphoteric surface-active agents, non-ionic wetting agents and macromolecular wetting agents. In the context of this invention, it is preferable to use anionic wetting agents.

Examples of anionic wetting agents are sodium lauryl sulphate, sodium cetyl stearyl sulphate, or sodium dioctyl sulphosuccinate. Sodium lauryl sulphate is the particularly preferred wetting agent.

An example of an amphoteric wetting agent is lecithin.

Examples of non-ionic wetting agents are cetyl alcohol, stearyl alcohol, cetyl stearyl alcohol, cholesterol, sorbitan fatty acid esters, such as sorbitan mono-oleate, polyoxyethylene sorbitan fatty acid esters, such as polysorbate 20, polyoxyethylene fatty acid glycerides, such as macrogol 1000 glycerol monostearate, polyoxyethylene fatty acid esters, such as polyoxyl 40 stearate, polyoxyethylene fatty alcohol ethers, such as polyoxyl 10 oleyl ether, or glycerol fatty acid esters, such as glycerol monostearate.

An example of a macromolecular wetting agent is Poloxamer 407.

The oral dosage form of the invention, preferably a tablet, may also contain pharmaceutical excipients, e.g. additives to improve the powder flowability. One example of an additive to improve the powder flowability is disperse silica, e.g. known under the trade name Aerosil®. Preferably, silica is used with a specific surface area of 50 to 400 m²/g, particularly preferably 100 to 250 m²/g, determined by gas adsorption in accordance with Ph. Eur., 6th edition 2.9.26., Method 1.

Additives to improve the powder flowability are generally used in an amount of 0.05 to 5% by weight, e.g. 0.1 to 4% by weight, based on the total weight of the formulation.

In addition, lubricants can be used as further excipients. Lubricants are generally used in order to reduce sliding friction. In particular, the intention is to reduce the sliding friction found during tablet pressing between the punches moving up and down in the die and the die wall, on the one hand, and between the edge of the tablet and the die wall, on the other hand. Suitable lubricants are, for example, stearic acid, adipic acid, sodium stearyl fumarate (Pruv®) and/or magnesium stearate.

Lubricants are normally used in an amount of 0.1 to 5% by weight, more preferably 1.0 to 4% by weight, based on the total weight of the formulation.

Anti-stick agents can be used in addition. "Anti-stick agents" is usually understood to mean substances which reduce agglomeration in the core bed. Examples are talcum, silica gel, polyethylene glycol (preferably with 2,000 to 10,000 g/mol weight-average molecular weight) and/or glycerol monostearate.

It lies in the nature of pharmaceutical excipients that they sometimes perform more than one function in a pharmaceutical formulation. In the context of this invention, in order to provide an unambiguous delimitation, the fiction will therefore preferably apply that each substance can only perform one function. This means that a substance which is used as a particular excipient is not simultaneously also used as a further pharmaceutical excipient. Microcrystalline cellulose—if used as a wicking agent—is not also used as a filler, for example (even though microcrystalline cellulose also exhibits a filling effect). To put it another way, two excipients with different functions, e.g. wicking agents and lubricants, should be different from one another in material terms, i.e. they should be formed from different substances.

In a preferred embodiment, the oral dosage form of the invention has a two-phase structure. This means that the oral composition of the invention is preferably built of
(i) an inner granular phase, containing
(a1) deferasirox;
(b1) binder;
(c1) disintegrant;
(d1) optionally wicking agent;
(e1) optionally filler;
(f1) optionally wetting agent; and
(ii) an outer phase, containing
(c2) disintegrant;
(d2) optionally wicking agent; and
(e2) optionally filler;
wherein the weight ratio deferasirox (a):disintegrant (c1+c2) is especially 1.0:1.0 to 1.0:3.0, preferably 1.1:2.5, more preferably 1.2:2.0. When introduced into water, the two-phase composition of the invention preferably leads to a suspension with the above-mentioned particle size distribution.

The two-phase dosage form of the invention preferably contains
(i) in the inner granular phase,
(a1) 10 to 50% by weight, more preferably 20 to 35% by weight, deferasirox;
(b1) 1 to 25% by weight, more preferably 2 to 10% by weight, binder;
(c1) 5 to 35% by weight, preferably 10 to 30% by weight, disintegrant;
(d1) 0 to 20% by weight wicking agent;
(e1) 0 to 30% by weight, more preferably 5 to 20% by weight, filler;
(f1) 0 to 5% by weight, more preferably 0.5 to 3% by weight, wetting agent; and (ii) in the outer phase,
(c2) 5 to 35% by weight, preferably 10 to 30% by weight disintegrant;
(d2) 0 to 25% by weight, more preferably 5 to 20% by weight, wicking agent; and
(e2) 0 to 30% by weight, more preferably 5 to 20% by weight, filler;

All the statements of % by weight relate here to the total weight of the dosage form. Reference is made to the above explanations with regard to the preferred embodiments of components (b) to (f).

The two-phase oral dosage form of the invention is preferably produced using a specific wet granulation process or especially with a melt granulation process.

The subject matter of the invention is therefore a method of producing an oral dosage form built of
(i) an inner granular phase, containing
(a1) deferasirox;
(b1) binder;
(c1) disintegrant;
(d1) optionally wicking agent;
(e1) optionally filler;
(f1) optionally wetting agents; and
(ii) an outer phase, containing
(c2) disintegrant;
(d2) optionally wicking agent; and
(e2) optionally filler;
comprising the steps of
(I) granulating components (a1), (b1) and (c1) and optionally (d1), and (f1);
(II) preferably mixing the granules resulting from step (I) with components (c2) and optionally (d2) and (e2);
(III) converting the mixture from step (II), optionally with the addition of further pharmaceutical excipients, into an oral dosage form.

With regard to the type and amounts of components (a) to (f) used in the method of the invention, reference is made to the above explanations concerning the oral dosage form of the invention.

In a preferred embodiment, step (I) is a melt processing step, especially a melt granulation step.

In one embodiment of the present invention, in the course of melt processing (a), deferasirox is processed with the—preferably thermoplastic—binder (b1) and disintegrant (c1), and optionally wicking agent (d1), filler (e1) and wetting agents (f1) in such a way that deferasirox is embedded in the excipients. In this connection, it is preferably for the melting conditions to be selected such that the excipients are melted or partially melted, whereas the active agent remains in a solid state. Deferasirox is preferably used in this context in crystalline form, and the melting conditions are preferably selected such that the active agent remains in crystalline form.

The temperature chosen during the melt processing is preferably from 10° C. below to 10° C. above the melting point of the binder, preferably with the proviso that the temperature chosen is at least 10° C. below the melting temperature of the deferasirox used.

The melt processing can preferably be carried out as melt granulation or melt extrusion.

In a preferred embodiment, melt granulation is performed. In this case, the melting process is preferably performed by means of an intensive mixer with a heatable jacket unit; a Diosna® P1-6, for example, can advantageously be used. In this context, it is usual for the mixture of components (a1) to (c1) and optionally (d1) to (f1) to be pre-mixed in a dry state without heating the jacket and then heated up in a second step by switching on the heatable jacket, preferably with stirring.

The heating is preferably continued until an increase in the power consumption is observed. After that, the mixture is granulated and cooled. In melt granulation, a temperature of 50 to 260° C., preferably 60 to 250° C., more preferably 70 to 220° C., even more preferably 80 to 200° C., especially 90 to 180° C., is chosen.

In a different preferred embodiment, melt extrusion is performed. This is a continuous method (independent of batches), where the pre-mixing and granulating are not performed sequentially in time, but rather in one production step. A preferred method of preparing the melt extrudate is melt extrusion by means of a twin-screw extruder (e.g. Leistritz® micro 18). It is an advantage here that setting a temperature gradient, depending on the matrix former chosen, allows the dwell time of the deferasirox at high temperatures to be reduced considerably. The temperature gradient is usually between 80-190° C. and is preferably selected such that after processing, the deferasirox is still present in crystalline form if this is desired in the context of the first embodiment. In a subsequent optional step, the extruded material can be granulated. The granulating may take place before, during or after cooling.

Apart from melt processing or melt granulation, other granulation techniques may also be used. "Granulating" is generally understood to mean the formation of relatively coarse or granular aggregate material as a powder by assembling and/or aggregating finer powder particles (agglomerate formation, or build-up granulation) and/or the formation of finer granules by breaking up coarser aggregates (disintegration, or breakdown granulation). Granulation can conventionally mean wet or dry granulation. Dry granulation is generally carried out using pressure or temperature. Wet granulation is generally carried out using binder solutions. Granulation is generally carried out in conventional granulating devices, such as extruder, perforated-disk, perforated-roll, or fluidised-bed granulators. Compulsory mixers or spray dryers can likewise be used.

In an alternative preferred embodiment, the granulation takes the form of wet granulation.

Step (I) therefore preferably comprises the stages of
(I-1) suspending components (a1), (b1) and optionally (f1) in a solvent, and
(I-2) applying the suspension under granulation conditions to components (c1) and optionally (d1) and (e1).

Suitable solvents in step (I-1) are water and/or organic solvent. Preferably, for example, water, ethanol or a mixture thereof is used.

Step (I-2) can be carried out in the granulating devices explained above. It is preferably carried out in a fluidised bed. In a preferred embodiment, the wet granulation is therefore carried out in a fluidised bed granulator, such as a Glatt® GPCG 3 (Glatt GmbH, Germany). The granulating time is usually 1 minute to 1 hour, preferably 2 minutes to 30 minutes.

In granulation step (I) (both in the case of wet granulation and in the case of melt processing), the granulation conditions are selected in a preferred embodiment such that the resulting particles (granules) have a weight-average particle size (D50 value) of 25 to 800 µm, more preferably 50 to 400 µm, even more preferably 80 to 500 µm, especially 110 to 220 µm. The weight-average particle size is determined by means of screen analysis (using a Retsch® AS 2000, amplitude 1.5 sec., interval 10 min., amount of sample 15.8 g).

In addition, the granulation conditions are preferably selected such that the resulting granules have a bulk density of 0.3 to 0.85 g/ml, more preferably 0.4 to 0.8 g/ml, especially 0.5 to 0.7 g/ml. The Hausner factor is usually in the range from 1.02 to 1.3, more preferably from 1.03 to 1.25 and especially from 1.04 to 1.15. The "Hausner factor" in this context means the ratio of tapped density to bulk density. The bulk density and tapped density are determined in accordance with USP 24, test 616 "Bulk Density and Tapped Density".

In the optional step (II) of the method of the invention, the granules resulting from step (I) are preferably mixed with components (c2) and optionally (d2) and (e2). The mixing may, for example, be performed in conventional mixing devices, such as a free-fall mixer—e.g. in a Turbula® T10B (Bachofen AG, Switzerland). The mixing time may, for example, be 1 minute to 20 minutes, preferably 5 to 15 minutes.

In step (III) of the method of the invention, the mixture obtained in step (II) is preferably pressed into tablets, i.e. the step involves compression into tablets. The compression can be performed with tableting machines known in the state of the art, such as eccentric presses or rotary presses. In the case of rotary presses, a compressive force of 2 to 40 kN, preferably 2.5 to 35 kN, is usually applied. As an example, the Fette® 102i press (Fette GmbH, Germany) is used. In the case of eccentric presses, a compressive force of 1 to 20 kN, preferably 2.5 to 10 kN, is usually applied. By way of example, the Korsch® EK0 is used.

In step (III) of the method of the invention, pharmaceutical excipients may be added to the mixtures from step (II). On this subject, reference may be made to the above explanations on suitable excipients.

The subject matter the invention is not only the method of the invention, but also the oral dosage forms, especially tablets, produced with that method.

The tablets produced by the method of the invention may be tablets which can be swallowed unchewed (non-film-coated or preferably film-coated). They may likewise be chewable tablets. They are preferably dispersible tablets. "Dispersible tablet" here means a tablet to be used for producing an aqueous suspension for swallowing.

The tableting conditions are preferably selected such that the resulting tablets have a hardness of 40 to 200 N, particularly preferably 60 to 150 N.

In addition, the resulting tablets preferably have a friability of less than 3%, particularly preferably less than 1%, especially less than 0.8%. The friability is determined in accordance with Ph. Eur. 6.0, section 2.9.7.

In addition, the oral dosage forms of the invention, especially tablets, have a high uniformity of the content of active agent. In order to determine the uniformity of the oral dosage forms, 20 individual samples are taken from a batch at random. The uniformity of the content of active agent is then determined in accordance with Ph. Eur. 6.0, Chapter 2.9.6, HPLC being used as the analytical method. It is preferable for each of twenty dosage forms, especially tablets, to have a deferasirox content of between 90% and 110%, preferably 92% to 108%, even more preferably 94% to 106%, particularly preferably 96% to 104% and especially 98% to 102% of the average content of those twenty dosage forms.

As an alternative to compression into tablets, the granules resulting in steps (I) or (II) of the method of the invention may also be processed—optionally with the addition of further pharmaceutical excipients—into a particulate dosage form, such as by filling into capsules or sachets.

Finally, the invention relates to the use of deferasirox granulated with disintegrants for the preparation of an aqueous suspension, wherein the solid particles of the suspension have an average particle size (D50) of 20 µm to 120 µm.

The invention will now be illustrated with reference to the following examples.

EXAMPLES

Example 1

| Active agent + excipients | [mg/DF] | [%/DF] | Amount weighed in [g/batch] |
|---|---|---|---|
| Deferasirox | 125.00 | 29.40 | 6.25 |
| Lactose | 72.60 | 17.08 | 3.63 |
| Crospovidone | 63.70 | 14.98 | 3.19 |
| Polyvinyl pyrrolidone (PVP, Mw 12,500) | 12.80 | 3.01 | 0.64 |
| Sodium lauryl sulphate (SDS) | 2.10 | 0.49 | 0.11 |
| Crospovidone | 21.30 | 5.01 | 1.07 |
| Microcrystalline cellulose (MCC) | 48.30 | 11.36 | 2.42 |
| Maize starch | 78.30 | 18.42 | 3.92 |
| Disperse SiO$_2$ | 0.90 | 0.21 | 0.05 |
| Sodium stearyl fumarate | 0.10 | 0.02 | 0.01 |

Example 1a

Wet Granulation

PVP and SDS were dissolved in water. Deferasirox was suspended in the solution and used for the wet granulation of lactose and crospovidone. The granules were dried for 1 hour at 40° C. and then blended with a mixture of crospovidone, MCC, maize starch and disperse SiO$_2$. Sodium stearyl fumarate was added, and the entire mixture was blended before being pressed on an eccentric press.

In proportion to the dose, tablets were produced with strengths of 250 mg and 500 mg.

Example 1b

Melt Granulation

For the melt granulation process, deferasirox, lactose, MCC, maize starch, 50% crospovidone and PVP were partially melted in a high-shear mixer at more than 100° C. The granules were screened, after which SDS, the remainder of the crospovidone, disperse SiO$_2$ and sodium stearyl fumarate were added and then mixed for 3 minutes in a freefall mixer (Turbula® W10B), after which the mixture was compressed into tablets.

Example 2

| Active agent + excipients | [mg/DF] | [%/DF] | Amount weighed in [g/batch] |
|---|---|---|---|
| Deferasirox | 125.00 | 29.40 | 1.25 |
| Lactose | 72.60 | 17.08 | 0.73 |
| Crospovidone | 63.70 | 14.98 | 0.64 |
| Polyvinyl pyrrolidone (Mw 12,500) | 12.80 | 3.01 | 0.13 |
| SDS | 2.10 | 0.49 | 0.02 |
| Crospovidone | 21.30 | 5.01 | 0.21 |
| MCC | 41.30 | 9.72 | 0.41 |

| Active agent + excipients | [mg/DF] | [%/DF] | Amount weighed in [g/batch] |
|---|---|---|---|
| Na carboxymethyl cellulose | 85.30 | 20.07 | 0.85 |
| Disperse SiO$_2$ | 0.90 | 0.21 | 0.01 |
| Sodium stearyl fumarate | 0.10 | 0.02 | 0.00 |

Example 2a

Wet Granulation

PVP and SDS were dissolved in water. Deferasirox was added to the solution and suspended. The suspension was used for the granulation of lactose and crospovidone. The granules were dried for 1 hour in a drying cabinet at 40° C. and then blended with a mixture of crospovidone, MCC, sodium carboxymethyl cellulose and disperse SiO$_2$. Sodium stearyl fumarate was added, and the entire mixture was blended before being pressed on an eccentric press.

In proportion to the dose, tablets were produced with strengths of 250 mg and 500 mg.

Example 2b

Melt Granulation

For the melt granulation process, deferasirox, lactose, MCC, sodium carboxymethyl starch, 50% of the crospovidone and PVP were partially melted in a high-shear mixer at more than 100° C. The granules were screened, after which SDS, the remainder of the crospovidone, disperse SiO$_2$ and sodium stearyl fumarate were added and then mixed for 3 minutes in a free-fall mixer (Turbula® W10B), before being compressed into tablets.

Example 3

| Active agent + excipients | [mg/DF] | [%/DF] | Amount weighed in [g/batch] |
|---|---|---|---|
| Deferasirox | 125.00 | 29.45 | 1.25 |
| Lactose | 72.60 | 17.10 | 0.73 |
| Crospovidone | 63.70 | 15.01 | 0.64 |
| Polyvinyl pyrrolidone (Mw 12,500) | 12.80 | 3.02 | 0.13 |
| SDS | 2.10 | 0.49 | 0.02 |
| Crospovidone | 21.30 | 5.02 | 0.21 |
| Sodium carboxymethyl cellulose | 86.00 | 20.26 | 0.86 |
| Spray-dried lactose (monohydrate) | 40.00 | 9.42 | 0.40 |
| Disperse SiO$_2$ | 0.90 | 0.21 | 0.01 |
| Sodium stearyl fumarate | 0.10 | 0.02 | 0.00 |

Example 3a

Wet Granulation

PVP and SDS were dissolved in water. Deferasirox was suspended in the solution and used for the wet granulation of lactose and crospovidone. The granules were dried for 1 hour in a drying cabinet at 40° C. and then blended with a mixture of crospovidone, MCC, spray-dried lactose, sodium carboxymethyl cellulose and disperse SiO$_2$. Sodium stearyl fumarate was added, and the entire mixture was blended before being pressed on an eccentric press.

In proportion to the dose, tablets were produced with strengths of 250 mg and 500 mg.

Example 3b

Melt Granulation

For the melt granulation process, deferasirox, lactose, spray-dried lactose, 50% of the crospovidone and PVP were partially melted in a high-shear mixer at more than 100° C. The granules were screened, after which SDS, the remainder of the crospovidone, disperse SiO$_2$ and sodium stearyl fumarate were added and mixed for 3 minutes in a free-fall mixer (Turbula® W10B), before being compressed into tablets.

Example 4

| Active agent + excipients | [mg/DF] | [%/DF] | Amount weighed in [g/batch] |
|---|---|---|---|
| Deferasirox | 125.00 | 29.40 | 1.25 |
| Lactose | 72.60 | 17.08 | 0.73 |
| Crospovidone | 63.70 | 14.98 | 0.64 |
| Polyvinyl pyrrolidone (Mw 12,500) | 12.80 | 3.01 | 0.13 |
| SDS | 2.10 | 0.49 | 0.02 |
| Crospovidone | 21.30 | 5.01 | 0.21 |
| MCC | 36.30 | 8.54 | 0.36 |
| Sodium carboxymethyl starch | 30.00 | 7.06 | 0.30 |
| Alginic acid | 60.30 | 14.18 | 0.60 |
| Disperse SiO$_2$ | 0.90 | 0.21 | 0.01 |
| Sodium stearyl fumarate | 0.10 | 0.02 | 0.00 |

Example 4a

Wet Granulation

PVP and SDS were dissolved in water. Deferasirox was added to the solution and used for the wet granulation of lactose and crospovidone. The granules were dried for 1 hour in a drying cabinet at 40° C. and then blended with a mixture of crospovidone, MCC, alginic acid and disperse SiO$_2$. Sodium stearyl fumarate was added, and the entire mixture was blended before being pressed on an eccentric press.

In proportion to the dose, tablets were produced with strengths of 250 mg and 500 mg.

Example 4b

Melt Granulation

For the melt granulation process, deferasirox, lactose, MCC, alginic acid, 50% of the crospovidone and PVP were partially melted in a high-shear mixer at more than 100° C. The granules were screened, after which SDS, the remainder of the crospovidone, disperse SiO$_2$ and sodium stearyl fumarate were added and mixed for 3 minutes in a freefall mixer (Turbula® W10B), before being compressed into tablets.

Example 5

Production of a Suspension

In order to determine the particle size specified, the tablet of the invention in accordance with Example 1a was dissolved in 150 ml water (Aqua purificata in accordance with Ph. Eur) at 25° C. The particle size was determined 5 minutes after the dosage form was introduced into the water. During those 5 minutes, the suspension was stirred at 50 revolutions per minute.

When the particle size was measured, a D50 value of 70 μm was found.

The invention claimed is:

1. An oral dosage form, comprising
   (a) deferasirox,
   (b) binder,
   (c) disintegrant, and
   (d) optionally wicking agent
   wherein introducing the dosage form into water leads to a suspension wherein the suspended particles have an average particle size (D50) of 45 μm to 120 μm, wherein the average particle size is determined 5 minutes after the dosage form is introduced into water by means of laser diffractometry, and wherein the dosage form comprises 42% to 60% by weight (c), based on the total weight of the dosage form.

2. The oral dosage form of claim 1, wherein the weight ratio deferasirox:disintegrant is 1:1 to 1:3.

3. The oral dosage form of claim 1, containing 5 to 25% wicking agent (d), based on the total weight the dosage form.

4. The oral dosage form of in claim 1, wherein the binder (b) has a viscosity of 1 to 50 mPa·s in a 2% solution.

5. The oral dosage form of claim 1, produced by means of melt processing.

6. The oral dosage form of claim 1, comprising
   (i) an inner granular phase, comprising
      (a1) deferasirox;
      (b1) binder;
      (c1) disintegrant;
      (d1) optionally wicking agent;
      (e1) optionally filler;
      (f1) optionally wetting agent; and
   (ii) an outer phase, comprising
      (c2) disintegrant;
      (d2) optionally wicking agent; and
      (e2) optionally filler.

7. The oral dosage form of claim 1 in the form of a tablet with a disintegration time of 10 to 90 seconds.

8. A method of preparing an oral dosage form according to claim 1 comprising
   (i) an inner granular phase, comprising
      (a1) deferasirox;
      (b1) binder;
      (c1) disintegrant;
      (d1) optionally wicking agent;
      (e1) optionally filler;
      (f1) optionally wetting agent; and
   (ii) an outer phase, comprising
      (c2) disintegrant;
      (d2) optionally wicking agent; and
      (e2) optionally filler;
   comprising the steps of:
      (I) granulating components (a1), (b1) and (c1) and optionally (d1), and (f1);
      (II) mixing the granules resulting from step (I) with components (c2) and optionally (d2) and (e2)
      (III) converting the mixture from step (II), optionally with the addition of further pharmaceutical excipients, into an oral dosage form.

9. The method of claim 8, wherein step (I) is a melt granulation step and is carried out at temperatures of 60° C. to 250° C.

10. The method of claim 8, wherein step (I) is a wet granulation step comprising
    (I-1) suspending components (a1), (b1) and optionally (f1) in a solvent, and
    (I-2) applying the suspension under granulation conditions to components (c1) and optionally (d1) and (e1).

11. The method of claim 8, wherein granulation conditions in step (I) are selected such that the resulting particles have an average particle size of 80 μm to 250 μm.

12. The method of claim 8, wherein components (c1) and (c2) together are present in an amount from 42% to 60% by weight, based on the total weight the oral dosage form.

13. The method of claim 8, wherein step (III) includes filling into capsules or sachets or compressing into tablets.

14. The oral dosage form of claim 1, wherein the dosage form comprises 45% to 55% by weight disintegrant (c), based on the total weight of the dosage form.

15. The oral dosage form of claim 1, wherein the weight ratio deferasirox:disintegrant is 1.0:1.1 to 1.0:2.5.

16. The oral dosage form of claim 15, wherein the weight ratio deferasirox:disintegrant is 1.0:1.2 to 1.0:2.0.

17. The oral dosage form of claim 1, wherein the suspended particles have an average particle size (D50) of 55 μm to 100 μm.

18. The oral dosage form of claim 17, wherein the suspended particles have an average particle size (D50) of 65 μm to 90 μm.

19. The oral dosage form of claim 1, wherein
    the dosage form comprises 45% to 55% by weight disintegrant (c), based on the total weight of the dosage form;
    the weight ratio deferasirox:disintegrant is 1.0:1.2 to 1.0:2.0;
    the suspended particles have an average particle size (D50) of 65 μm to 90 μm; and
    the disintegrant (c) is selected from carrageenan, alginic acid, sodium alginate, maize starch, pregelatinised starch, sodium carboxymethyl starch, calcium carboxymethyl starch, crosslinked carboxymethyl cellulose, and bentonites.

* * * * *